(12) United States Patent
Bhatnagar et al.

(10) Patent No.: US 7,279,480 B2
(45) Date of Patent: Oct. 9, 2007

(54) HEXAHYDROPYRIDAZINE-3-CARBOXYLIC ACID HYDRAZIDE AND HYDRAZONE DERIVATIVES, COMBINATORIAL LIBRARIES CONTAINING SAME, PHARMACEUTICAL COMPOSITIONS CONTAINING SAME AND METHODS OF PREPARATION

(75) Inventors: Neerja Bhatnagar, Neshanic Station, NJ (US); Pierre Broto, Romainville (FR); Jean-Francois Gourvest, Claye Souilly (FR); Jacques Mauger, Tucson, AZ (US)

(73) Assignee: Aventis Pharma S.A., Paris (FR)

( * ) Notice: Subject to any disclaimer, the term of this patent is extended or adjusted under 35 U.S.C. 154(b) by 260 days.

(21) Appl. No.: 11/009,249

(22) Filed: Dec. 10, 2004

(65) Prior Publication Data

US 2005/0215553 A1    Sep. 29, 2005

Related U.S. Application Data

(63) Continuation of application No. PCT/FR03/01770, filed on Jun. 12, 2003.

(30) Foreign Application Priority Data

Jun. 14, 2002  (FR) .................................. 02 07346

(51) Int. Cl.
  *C07D 237/04*   (2006.01)
  *A61K 31/501*   (2006.01)
  *A61K 31/50*    (2006.01)

(52) U.S. Cl. ................. 514/247; 514/252.01; 544/224; 544/238

(58) Field of Classification Search ................ 544/238, 544/224; 514/247, 252.01
See application file for complete search history.

(56) References Cited

OTHER PUBLICATIONS

Cecil Textbook of Medicine (20th Edition, vol. 2, 1996, pp. 1736-1747.*
Hale, K. J., Synthetic Route to the GE3 Cyclodepsipeptide, Organic Letters, vol. 4, No. 11, 2002, pp. 1903-1906.
Hale, K. J. , Asymmetric Total Synthesis of Antitumor Antibiotic A83586C, Chemical Communications, vol. 23, 1997, pp. 2319-2320.
Leung, D. et al, Protease Inhibitors: Current Status and Future Prospects, Journal of Medicinal Chemistry, vol. 43, No. 3; Feb. 2000, pp. 305-341.

* cited by examiner

Primary Examiner—Kahsay Habte
(74) Attorney, Agent, or Firm—Balaram Gupta

(57) ABSTRACT

The present invention discloses and claims hexahydropyridazine-3-carboxylic acid hydrazides and hydrazones of formula (I)

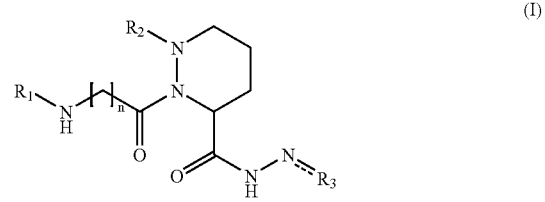

as inhibitors of proteases and kinases, and methods of using said compounds of formula (I) for the prevention or treatment of certain cardiovascular, central nervous system, inflammatory, and bone diseases as well as infectious diseases and certain cancers. Combinatorial libraries of the compounds of formula (I), pharmaceutical compositions, and methods for the preparation of combinatorial libraries and the compounds of formula (I) are also disclosed and claimed.

23 Claims, No Drawings

HEXAHYDROPYRIDAZINE-3-CARBOXYLIC ACID HYDRAZIDE AND HYDRAZONE DERIVATIVES, COMBINATORIAL LIBRARIES CONTAINING SAME, PHARMACEUTICAL COMPOSITIONS CONTAINING SAME AND METHODS OF PREPARATION

This application is a continuation of International Application No. PCT/FR03/01770 filed Jun. 12, 2003, which claims the benefit of priority of French Application No. 02 07346, filed Jun. 14, 2002, both of which are incorporated herein by reference in their entirety.

BACKGROUND OF THE INVENTION

1. Field of the Invention

The invention relates to novel hexahydropyridazine-3-carboxylic acid hydrazide or hydrazone derivatives, to the combinatorial libraries containing them, to the preparation thereof, to the use thereof as medicinal products, in particular as cathepsin K inhibitors, and also to the pharmaceutical compositions containing them.

2. Description of the Art

Metabolic enzymes such as proteases or kinases are enzymes that are widely distributed in the animal kingdom. By way of nonexhaustive examples, mention may be made, as bibliographical references for proteases, of the documents: "Methods in Enzymology XLII (1975)" and "Journal of Medicinal Chemistry" vol. 43 n°3 (D. Leung, G. Abbenante and D. P. Fairlie) and for kinases, the document: "Methods in Enzymology", Vol 80 (1981) (Academic Press Inc.).

Among the proteases capable of selectively catalyzing the hydrolysis of polypeptide bonds, mention may be made of the four main classes: aspartic protease, serine protease, cysteine protease and metalloprotease.

Aspartic proteases that may be mentioned include in particular HIV-1 protease, renin, plasmepsins and cathepsin D.

Serine proteases that may be mentioned include in particular thrombin, factor Xa, elastase, tryptase, "convertase complements" and hepatitis C NS3 protease.

Among the cysteine proteases, there are three structurally distinct groups: the papain and cathepsin group, the ICE group (caspases) and the picornaviral group (similar to the serine proteases, in which the serine is replaced with a cysteine).

Thus, mention may in particular be made of cathepsin K, cathepsin B, cathepsin L, cathepsin S, caspases, rhinovirus 3C protease, and the papains and calpains.

Metalloproteases that may be mentioned include in particular angiotensin-converting enzyme, neutral endopeptidase and a mixture of the two, matrix metalloprotease and tumor necrosis factor-α-converting enzyme.

These kinase or protease enzymes are involved in intercellular and intracellular catabolization and communication processes: they play an important role in a large number of diseases in different fields, such as in particular the cardiovascular field, oncology, the central nervous system, inflammation, osteoporosis and also infectious, parasitic, fungal or viral diseases. For this reason, these proteins are targets of great interest for pharmaceutical research.

All of the aforementioned references are incorporated herein by reference in their entirety.

SUMMARY OF THE INVENTION

A subject of the present invention is thus a compound of formula (I):

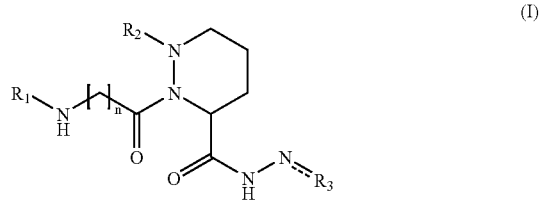

in which:

n is an integer from 0 to 6 inclusive;

$R_1$ represents a group chosen from:
  C(O)—$(CH_2)_m$—R
  C(O)—NH—$(CH_2)_m$—R or C(S)—NH—$(CH_2)_m$—R
  $SO_2$—$(CH_2)_m$—R in which
  m is an integer from 0 to 6 inclusive; it being possible for a double bond to be optionally present when n is greater than 2;

R is one of the groups:
  hydrogen when m is other than 0;
  hydroxyl or thiol;
  cyano;
  linear or branched alkoxy containing from 1 to 6 carbon atoms or aryloxy or aralkoxy;
  cycloalkyl having from 3 to 6 carbon atoms;
  a saturated or unsaturated, monocyclic or bicyclic, heterocyclic group;
    the ring of the heterocyclic radical being optionally substituted with one to three substituents chosen from: OH, SH, $NH_2$, $NO_2$, cyano, carboxyl, carbamoyl, halogen, trifluoromethyl, linear or branched alkyl containing from 1 to 6 carbon atoms, linear or branched alkoxy containing from 1 to 6 carbon atoms, acyl containing from 2 to 6 carbon atoms, aryl or aralkyl, a saturated or unsaturated, monocyclic or bicyclic heterocycle,
      these alkyl or aryl or aralkyl or heterocyclic radicals being themselves optionally substituted with one to three substituents chosen from: OH, SH, $NH_2$, $NO_2$, cyano, carboxyl, carbamoyl, halogen, trifluoromethyl,
  an aryl group containing from 6 to 10 carbon atoms or an aralkyl group containing from 7 to 11 carbon atoms,
    the ring of the aryl or aralkyl radical being optionally substituted with one to three substituents chosen from: OH, SH, $NH_2$, $NO_2$, cyano, carboxyl, carbamoyl, halogen, trifluoromethyl, linear or branched alkyl containing from 1 to 6 carbon atoms, linear or branched alkoxy containing from 1 to 6 carbon atoms, acyl containing from 2 to 6 carbon atoms, a saturated or unsaturated, monocyclic or bicyclic heterocycle,
      these alkyl or heterocyclic radicals being themselves optionally substituted with one to three substituents chosen from: OH, SH, $NH_2$, $NO_2$, cyano, carboxyl, carbamoyl, halogen, trifluoromethyl;

a group $NR_4R_5$, $R_4$ being a hydrogen atom or a linear or branched alkyl group having from 1 to 6 carbon atoms, $R_5$ being a hydrogen atom or a linear or branched alkyl radical having from 1 to 6 carbon atoms or an aryl group;

$R_2$, which is identical or different, has the same meaning as $R_1$, or may represent hydrogen;

the side group:

represents $NH-R_3$ or $N=R_3$, in which
$R_3$, which is identical or different, has the same meaning as $R_1$, when this side group represents $NH-R_3$; and
$R_3$, which is identical or different, has the same meaning as $R$, when this side group represents $N=R_3$;

said products of formula (I) being in any of the possible racemic, enantiomeric and diastereoisomeric isomer forms;

and also the addition salts with inorganic and organic acids or with inorganic and organic bases of these products.

DETAILED DESCRIPTION OF THE INVENTION

According to one embodiment, n is 2.
According to one embodiment, $R_2$ represents hydrogen.
According to one embodiment, the side group

represents $NH-R_3$.
According to one embodiment, the side group

represents $N=R_3$.
According to one embodiment, the compounds of the present invention have the following stereochemistry:

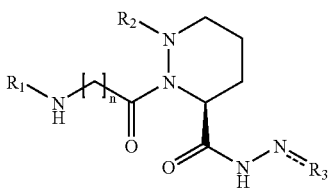

The compounds of the present invention as defined above and hereinafter have inhibitory properties with respect to metabolic enzymes as defined above, in particular with respect to kinases or to proteases, such as in particular cysteine proteases or serine proteases.

The compounds of the present invention may thus in particular be useful in the prevention or treatment of diseases in which such metabolic enzymes are involved, such as certain cardiovascular diseases, central nervous system diseases, inflammatory diseases, bone diseases such as, for example, osteoporosis, infectious diseases requiring in particular anti-infectious agents for the treatment thereof, or else certain cancers.

In the compounds of formula (I) and in the following text:
the bivalent group represented by $-(CH_2)_n-$ may be linear or branched;
the term "aryl" denotes an unsaturated radical containing from 6 to 10 carbon atoms comprising one or two fused rings, optionally containing one to three hetero atoms chosen from nitrogen, oxygen and sulfur. Mention may be made of: phenyl, naphthyl;
the term "aralkyl" denotes an aryl radical, as defined above, containing from 7 to 11 carbon atoms linked via a linear or branched alkyl radical, said alkyl radical having from 1 to 5 carbon atoms. Mention may in particular be made of benzyl;
the terms "alkoxy", "aryloxy" and "aralkyloxy" indicate the presence of a terminal oxygen on the alkyl, aryl or aralkyl group;
the term "monocyclic heterocyclic radical" denotes a saturated or unsaturated radical consisting of 5 or 6 ring-members such that one or more of the ring-members is an oxygen, sulfur or nitrogen atom. Such a heterocyclic radical thus denotes a carbocyclic radical containing one or more hetero atoms chosen from oxygen, nitrogen or sulfur atoms, it being understood that the heterocyclic radicals may contain one or more hetero atoms chosen from oxygen, nitrogen or sulfur atoms and that, when these heterocyclic radicals comprise more than one hetero atom, the hetero atoms of these heterocyclic radicals may be identical or different. Mention may in particular be made of the following radicals: dioxolane, dioxane, dithiolane, thiooxolane, thioxane, morpholinyl, piperazinyl, piperazinyl substituted with a linear or branched alkyl radical containing up to 4 carbon atoms, piperidyl, thienyl such as 2-thienyl and 3-thienyl, furyl such as 2-furyl, pyrimidinyl, pyridyl such as 2-pyridyl, 3-pyridyl and 4-pyridyl, pyrimidyl, pyrrolyl, thiazolyl, isothiazolyl, diazolyl, thiadiazolyl, triazolyl, free or salified tetrazolyl, thiadiazolyl, thiatriazolyl, oxazolyl, oxadiazolyl, or 3- or 4-isoxazolyl. Mention may most particularly be made of the following radicals: morpholinyl, thienyl such as 2-thienyl and 3-thienyl, furyl such as 2-furyl, tetrahydrofuryl, thienyl, tetrahydrothienyl, pyrrolyl, pyrrolinyl, pyridyl and pyrrolidinyl;
the term "bicyclic heterocyclic radical" denotes a saturated or unsaturated radical consisting of 8 to 12 ring-members such that one or more of the ring-members is an oxygen, sulfur or nitrogen atom and in particular condensed heterocyclic groups containing at least one hetero atom chosen from sulfur, nitrogen and oxygen, for example benzothienyl such as 3-benzothienyl, benzothiazolyl, quinolyl, tetralone, benzofuryl, benzopyrrolyl, benzimidazolyl, benzoxazolyl, thionaphthyl, indolyl or purinyl.

The compounds of formula (I) may be converted to salts (salified) by means known to those skilled in the art, among which mention may be made, for example, of:
among the salt forming (salification) compounds, inorganic bases such as, for example, an equivalent of sodium, of potassium, of lithium, of calcium, of magnesium or of ammonium or organic bases such as, for example, methylamine, propylamine, trimethylamine, diethylamine, triethylamine, N,N-dimethylethanolamine, tris(hydroxy-methyl)aminomethane, ethanolamine, pyridine, picoline, dicyclohexylamine, morpholine, benzylamine, procaine, lysine, arginine, histidine, N-methylglucamine;

the addition salts with inorganic or organic acids of the compounds of formula (I) may be, for example, the salts formed with hydrochloric acid, hydrobromic acid, hydriodic acid, nitric acid, sulfuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, the alkylmonosulfonic acids such as, for example, methanesulfonic acid, ethanesulfonic acid or propanesulfonic acid, the alkyldisulfonic acids such as, for example, methanedisulfonic acid, alpha, beta-ethanedisulfonic acid, the arylmonosulfonic acids such as benzenesulfonic acid, and the aryldisulfonic acids.

It may be recalled that the stereoisomerism can be defined in its broad sense compounds having the same structural formulae, but in which the various groups are arranged differently in space, such as in particular in monosubstituted cyclohexanes in which a substituent can be in the axial or equatorial position, and the various possible rotational conformations of ethane derivatives. However, another type of stereoisomerism exists, due to the different spatial arrangements of substituents fixed either on double bonds or on rings, which is often referred to as geometric isomerism or cis-trans isomerism. The term "stereoisomers" is used in the present application in its broadest sense and therefore relates to all the compounds indicated above.

As used herein, the term "rank" defines the number of dimensions for a matrix. The aforesaid matrix is comprised of at least two ranks or dimensions, wherein each rank is further comprised of at least two substituent groups as defined for one of the Markush groups of a compound of formula (I) of the invention, such as for example, $R_1$, $R_2$, $R_3$ or the like Markush groups. It is understood that the aforesaid matrix represents "individualized" or single compounds as defined by the combination of individual matrix row and column substituent groups, but mixtures of compounds may also be represented.

Combinatorial Libraries of Compounds According to the Invention

A subject of the present invention is thus also combinatorial libraries. These combinatorial libraries are in particular in the form of matrices of variable rank, the rank being at least 2, at least 2 ranks containing at least 2 compounds, each compound being individualized.

It is understood that these matrices may be made available in a form which is not necessarily of the same rank; thus, it is possible to obtain a matrix of rank 3 in the form of plates with test samples, the plates being of order 2. It is also understood that the matrices, for example of rank 3, when they are available in a form of order 3 or less, are not necessarily ordered.

The invention thus covers the combinatorial libraries in the form of sets comprising a plurality of compounds according to the invention, each compound being individualized. This set of compounds comprises in particular plates with wells each comprising a compound according to the invention. These sets comprise at least 4 individualized compounds according to the invention.

The combinatorial libraries according to the invention are in particular discrete.

The combinatorial libraries generally comprise a large number of compounds, typically of the order of about a hundred or of about a thousand.

These combinatorial libraries are used as a search tool for the purpose of screening for medicinal products. The compounds making up the combinatorial library show the pharmacological properties mentioned below.

Chemical Synthesis and Pharmacology

1. Chemical Methods According to the Invention

In the method according to the invention, the compounds are prepared in the form of combinatorial libraries, as indicated above. It is also possible to prepare them conventionally by carrying out the method compound by compound.

The method according to the invention thus comprises the following steps:

(i) coupling the compound of formula (II):

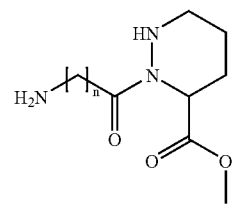

II in which n has the value indicated above, onto an immobilized support, to form an immobilized reactant of formula (III):

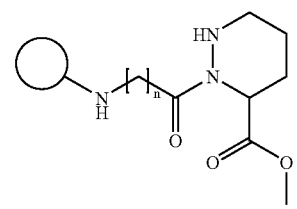

III in which the circle denotes the support;

(ii) reacting the compound of formula III with a compound of formula $R_1'$, $R_1'$ being a precursor of the group $R_1$, this precursor having the meaning corresponding to that of $R_1$ as indicated above, to form a compound of formula (IV):

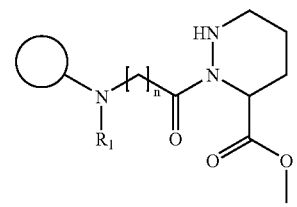

IV (iii) optionally reacting the compound of formula IV with a compound of formula $R_2'$, $R_2'$ being a precursor of the group $R_2$, this precursor having the meaning corresponding to that of $R_2$ as indicated above, to form a compound of formula (V):

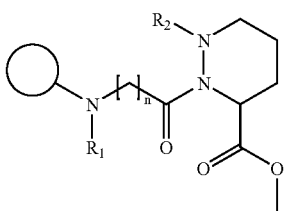

V (iv) reacting a compound of formula IV or V with. hydrazine to form the compound of formula (VI):

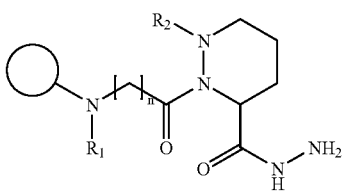

VI (v) reacting the compound of formula VI with a compound of formula $R_3'$, $R_3'$ being a precursor of the group $R_3$, this precursor having the meaning corresponding to that of $R_3$ as indicated above, to form a compound of formula (VII):

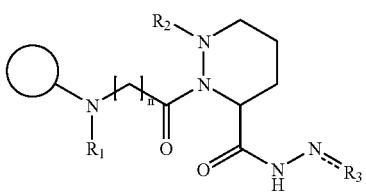

VII (vi) cleaving the compound of formula VII into the desired compound of formula I.

In the above, the $R_1'$, $R_2'$ and $R_3'$ reactants used are precursors. They react with the (secondary or primary) amino functions so as to result in the desired groups. In particular, the $R_1'$ and $R_2'$ precursors are chosen from acids, anhydrides, chlorides (acid, sulfonyl or carbamoyl chlorides), chloroformates, isocyanates and thioisocyanates. The same is true for the $R_3'$ precursor of $R_3$ when the $N-R_3$ bond is a single bond. When the $N=R_3$ bond is a double bond, the precursor is an aldehyde.

These reactions (ii), (iii) and (v) are carried out under conventional conditions, in relation to the reactions under consideration, known to those skilled in the art. For example, these reactions are conventionally carried out in an aprotic dipolar solvent in the presence of a base. When the $N=R_3$ bond is double, the aldehyde is reacted with hydrazides for example in a THF/methyl ortho-formate mixture.

The coupling reaction is carried out conventionally on a support of the resin type, for example by reductive amination (typically reaction of the primary amine on an aldehyde present on the basic resin; the reaction is carried out by addition of a suspension of product II in a dichloromethane/DMF mixture to the resin, followed by addition of sodium borohydride triacetate). The resin is a resin of the 4-formyl-3,5-dimethoxyphenoxy type (PL-FDMP, Polymer Laboratories StratoSpheres).

Formation of hydrazide VI is carried out conventionally by addition of hydrazine.

The cleavage reaction is carried out conventionally by the action of trifluoroacetic acid in dichloromethane (50/50).

The method according to the invention may also comprise one or more of the following optional reactions, in an appropriate order, so as to obtain the desired compound:
protection of the reactive functions,
deprotection of the reactive functions,
esterification,
saponification,
amidation,
acylation,
sulfonylation,
alkylation,
introduction of a double bond,
reduction of carboxylic acids,
salification,
ion exchange,
resolution or separation of diastereoisomers.

The optional steps are, in general, conventional reactions well known to those skilled in the art.

Thus, the reactive functions that it is advisable, where appropriate, to protect are generally carboxylic acid, amine, amide and hydroxyl functions.

The protection of the acid function is in particular carried out in the form of alkyl esters, or of allyl, benzyl, benzhydryl or p-nitrobenzyl esters.

The deprotection is carried out by saponification, acid hydrolysis, hydrogenolysis, or else cleavage by means of soluble palladium (0) complexes.

The protection of the amines and amides is in particular carried out in the form of benzyl derivatives, in the form of carbamates, in particular allyl, benzyl, phenyl or tert-butyl carbamates, or else in the form of silyl derivatives such as tert-butyl dimethyl-, trimethyl-, triphenyl- or else diphenyl-tert-butyl-silyl derivatives.

The deprotection is carried out, according to the nature of the protective group with sodium or lithium in liquid ammonia, by hydrogenolysis or by means of soluble palladium (0) complexes, by the action of an acid, or by the action of tetrabutylammonium fluoride.

The protection of the alcohols is carried out conventionally, in the form of ethers, of esters or of carbonates. The ethers may be alkyl or alkoxyalkyl ethers, preferably methyl or methoxyethoxymethyl ethers, aryl ethers or preferably aralkyl ethers, for example benzyl ethers, or silyl ethers, for example the silyl derivatives mentioned above. The esters may be any cleavable ester known to those skilled in the art, and preferably the acetate, the propionate or the benzoate or p-nitrobenzoate. The carbonates may be, for example, methyl, tert-butyl, allyl, benzyl or p-nitrobenzyl carbonates.

The deprotection is carried out by the means known to those skilled in the art, in particular saponification, hydrogenolysis, cleavage with soluble palladium (0) complexes, hydrolysis in acid medium or else, for the silyl derivatives, treatment with tetrabutylammmonium fluoride.

The amidation reaction is carried out, starting with the carboxylic acid, by means of an activating agent such as an alkyl chloroformate or EDCI, or by the action of aqueous ammonia or of an appropriate amine or of their acid salts.

Where appropriate, the acylation and sulfonylation reactions are carried out on the hydroxyureas by the action, respectively, of an appropriate carboxylic acid halide or anhydride or of an appropriate sulfonic acid halide.

The alkylation reaction is carried out by the action, on the hydroxyl derivatives, of an alkyl halide or an alkyl halide that is substituted, in particular with a free or esterified carboxyl radical.

Where appropriate, the possible final introduction of a double bond is carried out by the action of a halogenated derivative of selenium, and then oxidation, according to methods known to those skilled in the art.

Where appropriate, the reduction of acids to alcohols can be carried out by the action of a borane or via an intermediate mixed anhydride, by the action of an alkali borohydride. The mixed anhydride is prepared, for example, using an alkyl chloroformate.

The salt formation (salification) with acids is, where appropriate, carried out by addition of an acid in the soluble phase to the compound. The salt formation with bases can involve either the compounds comprising an acid function, in particular a carboxyl function, or those comprising a sulfoxy function or those comprising a heterocycle which is acid in nature. In the first case, the process is carried out by addition of an appropriate base such as those mentioned above. In the second case, the pyridinium salt is obtained directly during the action of the $SO_3$-pyridine complex and the other salts are obtained from this pyridinium salt. In either case, it is also possible to carry out the process by ion exchange on resin. Examples of salt formation appear hereinafter in the experimental section.

The separation of the enantiomers and diastereoisomers can be carried out according to techniques known to those skilled in the art, in particular chromatography.

For the synthesis of the combinatorial libraries, conventional techniques of combinatorial chemistry (with linear or nonlinear synthesis) are used. Mention may be made, for example, of the following documents, with no implied limitation: U.S. Pat. Nos. 5,324,483, 5,143,854, 5,010,175, 5,288,514, 5,549,974, WO-A-9209300 and WO-A-9502566; each which is incorporated herein by reference in its entirety.

IRORI® (Irori Corporation California, 11025 North Torrey Pines Road, Suite 100, La Jolla, Calif. 92037) technology (including directed sorting) is in particular used, steps (ii), (iii) and (v) being randomized with the available reactants $R_1'$, $R_2'$ and $R_3'$.

The individualized compounds are then subsequently recovered in flasks.

Salt formation with acids is, where appropriate, carried out by addition of an acid in solution to the compound. Salt formation with bases can involve either the compounds comprising an acid function, in particular a carboxyl function, or those comprising a sulfoxy function or those comprising a heterocycle which is acid in nature. In the first case, the process is carried out by addition of an appropriate base such as those mentioned above. In the second case, the pyridinium salt is obtained directly during the action of the $SO_3$-pyridine complex and the other salts are obtained from this pyridinium salt. In either case, it is also possible to carry out the process by ion exchange on resin. Examples of salt formation appear hereinafter in the experimental section.

The separation of enantiomers and diastereoisomers can be carried out according to techniques known to those skilled in the art, in particular chromatography.

Illustrations of such reactions defined above are given in the preparation of the examples described hereinafter.

2. Pharmacological Properties

The compounds of formula (I) as defined above, and also their addition salts with acids, have advantageous pharmacological properties.

The compounds of the present invention may thus have inhibitory properties with respect to one or more metabolic enzymes as defined above, in particular with respect to kinases or to proteases.

Certain compounds of formula (I) of the present invention as defined above may therefore in particular have inhibitory properties with respect to certain protein kinases or with respect to proteases.

Proteases of interest that may be targeted include cathepsins B, H, J, L, N, S, T, C, V W, K, O or O2; in particular those involved in diseases of cartilage and bone metabolism, and bone cancers, and most particularly cathepsin K.

The levels, the regulation and the activity of a certain number of protein kinases or proteases play a role in several human pathologies. The activity of a protein kinase or protease may in particular be associated with receptors having transmembrane domains or with intracellular proteins.

Certain kinases or proteases may play a role in the initiation, development and completion of cell cycle events and, thus, molecules which inhibit such kinases or proteases are capable of limiting unwanted cell proliferations such as those observed in cancers, psoriasis, fungal growth and parasitic infections (animals, protists): such molecules which inhibit these kinases or proteases are also capable of intervening in the regulation of neurodegenerative diseases such as Alzheimer's disease.

Certain compounds of formula (I) of the present invention may thus have antimitotic properties.

Certain compounds of formula (I) as defined above may, as kinase or protease inhibitors, have in particular the property of inhibiting osteoclast-mediated bone resorption. They may therefore be useful for the therapeutic or prophylactic treatment of diseases which are caused at least in part by an unwanted increase in bone resorption, for example, osteoporosis.

Certain compounds of formula (I) of the present invention may thus, for example, inhibit the enzymatic digestion of bone matrix collagen and thus bone resorption by the osteoclasts.

The bone diseases for which treatment or prevention requires the use of the compounds of formula (I) are in particular osteoporosis, hypercalcemia, osteopenia, for example caused by bone metastases, dental disorders, for example periodontitis, hyperparathyroidism, periarticular erosions in rheumatoid arthritis, Paget's disease, and osteopenia induced by immobilization. In addition, the compounds of formula (I) can be used to relieve, prevent or treat bone disorders which are caused by treatments, by glucocorticoids, therapies linked to the taking of steroids or of corticosteroids or by deficiencies in male or femal sex hormones.

All these disorders are characterized by a bone loss which is based on a faulty balance between bone formation and bone destruction and which can be favorably influenced by inhibiting the bone resorption by osteoclasts.

Certain compounds of formula (I) of the present invention may have, in addition to their specific kinase- or protease-inhibiting properties, advantageous cellular effects such as antiproliferative properties and in particular effects on apoptosis.

It is known, by virtue of the studies described in the literature, such as in WO 97/20842, which is incorporated herein by reference in its entirety, that relationships exist between the cell cycle and apoptosis. Among the pathways which lead to apoptosis, some are kinase-dependent or protease-dependent.

The compounds of the present invention are in particular useful for tumor therapy.

The compounds of the invention can thus also increase the therapeutic effects of commonly used antitumor agents.

The compounds of formula (I) of the present invention also have anti-mitotic and anti-neurodegenerative properties.

Certain compounds of the present invention may be inhibitors of vasoconstrictive and hypertensive effects and may thus produce an anti-ischemic effect, or alternatively may oppose stimulant effects on certain cell types, in particular smooth muscle cells, fibroblasts, neuronal cells and bone cells.

The compounds according to the present invention can thus be used in the treatment of diseases such as proliferative diseases, cancer, restenosis, inflammation, allergies, cardiovascular diseases or certain infectious diseases.

The compounds of the present invention can also be used in the treatment of certain gastrointestinal or gynecological disorders, and in particular for a relaxing effect on the uterus.

The compounds of formula (I) of the present application may thus possess advantageous pharmacological properties justifying their use in therapeutics.

A subject of the invention is thus also the compounds according to the invention, for their use as medicinal products intended for the prevention or treatment of the above mentioned diseases.

A subject of the invention is most particularly the pharmaceutical compositions containing, as active principle, at least one of the compounds according to the invention, in combination with a pharmaceutically acceptable carrier.

The pharmaceutical compositions of the present invention as defined above can be administered buccally, parenterally or locally by topical application to the skin and the mucus membranes, or by intravenous or intramuscular injection.

These compositions may be solid or liquid and may be provided in any of the pharmaceutical forms commonly used in human medicine, such as, for example, simple or sugar-coated tablets, pills, lozenges, gelatin capsules, drops, granules, injectable preparations, ointments, creams or gels. They are prepared according to the usual methods. The active principle may be incorporated therein in excipients that are conventionally used in these pharmaceutical compositions, such as talc, gum arabic, lactose, starch, magnesium stearate, cocoa butter, aqueous or nonaqueous vehicles, fatty substances of animal or plant origin, paraffin derivatives, glycols, various wetting agents, dispersants or emulsifiers, and preserving agents.

The usual dosage, which can be varied according to the product used, the individual treated and the condition in question, may be, for example, from about 0.05 to about 5 g per day in adults, or preferably from about 0.1 to about 2 g per day.

A subject of the invention is also the use of the compounds according to the invention, for producing medicinal products intended for the prevention or treatment of the above mentioned diseases.

EXAMPLES

The following examples illustrate the invention without limiting it. In these examples, the following abbreviations are used:

DCM: dichloromethane
DMF: N,N-dimethylformamide
DIEA: diisopropylethylamine
DIC: diisopropylcarbodiimide
TFA: trifluoroacetic acid
EtOAc: ethyl acetate
HOBt: 1-hydroxybenzotriazole hydrate Example 1

Synthesis of the Backbone

The backbone of formula II is prepared by synthesis from the intermediate hexahydropyridazino-3-carboxylic acid (see also the description as intermediate product in documents WO-A-9955724, WO-A-9722619 and EP-A-25941, each of which is incorporated herein by reference in its entirety).

a) Esterification of the Acid Function

The hexahydropyridazinic acid (40 g; 0.151 mol) is dissolved in 200 ml of methanol and cooled to 0° C. $SOCl_2$ (36 ml; 0.45 mol) is added dropwise. The solution becomes clear; the temperature is allowed to return very gradually to ambient temperature, and the solution is then refluxed for one hour. The mixture is poured onto a DCM(200 ml)/ice (500 g) /$NaHCO_3$(60 g) mixture. The aqueous phase is extracted with DCM. The organic phase is washed with a saturated $NaHCO_3$ solution and then dried over $MgSO_4$. A colorless oil is obtained (41 g; 99%) and is used as it is.

b) Amidation of the Amine Function (Coupling with Alanine).

N-[(Phenylmethoxy)carbonyl]-β-alanine (50 g; 0.183 mol) in solution in DCM/DMF (200 ml/20 ml) is cooled to 0° C.; $SOCl_2$ (25 ml; 0.32 mol) is added dropwise. The mixture is left at 0° C. for one hour with stirring. The corresponding chloride is thus obtained. The product obtained in step a) is dissolved in 150 ml of DCM at 0° C.; DIEA (33 ml; 0.19 mol) is then added, followed by the chloride obtained above. The mixture is left for 3 hours with stirring; the temperature very gradually returns to ambient temperature. The mixing is washed successively with saturated solutions of $NaHCO_3$, $KHSO_4$ and NaCl, and then dried over $MgSO_4$. A yellow oil is obtained, that is purified by chromatography (1300 g silica column; eluent: 90/10 DCM/EtOAc).

c) Deprotection of the Amine Functions by Hydrogenolysis

The compound obtained in step b) (26 g; 0.054 mol) is dissolved in 250 ml of DCM/250 ml of MeOH; Pd/C (2.7 g) is then added. The mixture is left for 12 hours under a pressure of between 1900 and 1950 mbar. The palladium is changed in the course of the reaction. The filtrate is evaporated to dryness. White crystals are obtained (8.5 g; 73%). LC-MS analysis confirms that it is indeed the desired compound of formula II (n=2).

The overall reaction scheme is represented below (Z representing the group $C_6H_5CH_2OC(O)$—).

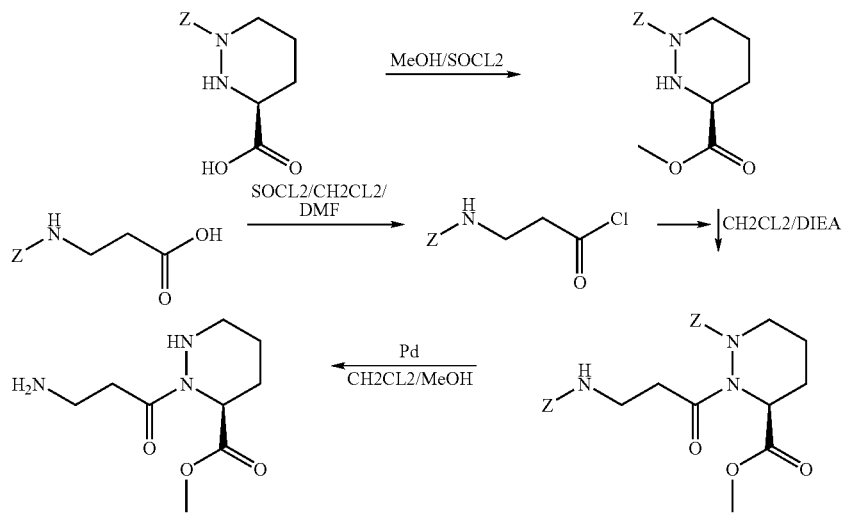

Example 2

Coupling on Resin

A 4-formyl-3,5-dimethoxyphenoxymethyl polystyrene resin is used. The resin (25 g, 1.5 mmol/g) is swollen in DCM (250 ml) and then filtered; it is then suspended in 200 ml of DCM plus 100 ml of DMF. The -substrate (compound to be grafted) (12 g; 0.056 mol) and $NaBH(OAc)_3$ (20 g; 0.094 mol) are then added. Gas is seen to be given off. The mixture is left for 4 hours with stirring and the resin is then filtered off and washed successively with 2×200 ml of DMF then 4× according to a cycle of 200 ml of DCM and 200 ml of MeOH, a last wash being carried out with 200 ml of ether. 35 g of grafted resin are obtained. The HR mass analysis is in agreement.

The product of formula (III) is then obtained, with, as coupled resin, the compound of formula (PS meaning polystyrene):

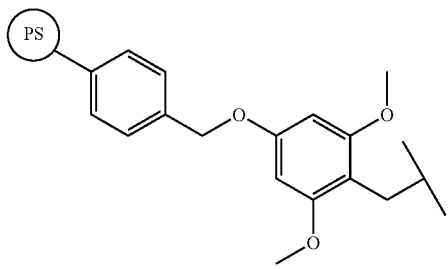

Example 3

Synthesis of a Combinatorial Library (rank 3; N—$R_3$ Single Bond). Combinatorial Library of Hydrazide-type Derivatives This synthesis is carried out in Irori® MiniKans. Each MiniKan contains 35 mg of resin, with a load of 1.2 mmol/g. 2.5 ml of solvent per MiniKan is envisaged during the reaction and the various washes. The MiniKans are dried under vacuum at 40° C. for 5 h after they have been washed.

a) First Randomization (Group $R_1$)

This is carried out in a variable manner depending on the reactants used. Each reactor contains 90 MiniKans in 250 ml of the reaction solvent.

Isocyanates, isothiocyanate: the reactant (5 eq) is added in DCM, followed by the DIEA (10 eq). Stirring is carried out at ambient temperature for 4 h, and the resin is then washed (DCM 2×250 ml; methanol/DCM 5×250 ml; ether 1×250 ml). The following reactants are used: trifluoromethylphenyl isocyanate, ethyl isocyanate and cyclopropyl isothiocyanate.

Acid anhydrides: the reactant (2 eq) is added in DCM followed by the DIEA (5 eq). Stirring is carried out at ambient temperature for 4 h and the resin is then washed (same cycle as above). The following reactants are used: acetic anhydride, isovaleric anhydride and 4-methoxybenzoic anhydride.

Sulfonyl chlorides: the conditions are the same as for the (thio)isocyanates. The following reactants are used: thiophene sulfonyl chloride, naphthalene sulfonyl chloride and mesitylene sulfonyl chloride.

b) Second Randomization (Group $R_2$)

This is carried out under the following conditions (included therein is a blank—in the case of $R_2$ hydrogen). Each reactor contains 90 MiniKans in 250 ml of the reaction solvent.

The acid chloride (10 eq) is added in DCM, followed by the DIEA (16 ml). Stirring is carried out at ambient temperature for 3 h and the resin is then washed (same protocol as above). The following reactants are used: acetyl chloride, butyryl chloride, furoyl chloride, methoxyacetyl chloride, methyl chloroformate and pentanoyl chloride.

The acid chloride (10 eq) is added in DCM, followed by pyridine (8 ml). Stirring is carried out at ambient temperature for 5 h and the resin is then washed (same protocol as above). The following reactants are used: benzoyl chloride and anisoyl chloride.

c) Formation of the Hydrazide

This is a common step. The 810 MiniKans are placed in 0.6 l of DMF and 0.2 l of hydrazine monohydrate. Stirring is carried out at ambient temperature for 15 h and the resin is then washed with 2×XDMF (0.6 1), and then 5×DCM/MeOH (1 1), 1×DCM (1 1) and 1×ether (1 1). The MiniKans are then dried.

d) Third Randomization (Group $R_3$).

This step is carried out in identical fashion to the first randomization step. Each reactor contains 81 MiniKans in 160 ml of the reaction solvent.

Acid chloride: The acid chloride (3 eq) is added in DCM, followed by pyridine (6 eq). Stirring is carried out at ambient temperature for 3 h and the resin is then washed (same protocol as above). The following reactants are used: piperonyl chloride, 4-morpholinecarbonyl chloride and N-methyl-N-phenylcarbamoyl chloride.

Sulfonyl chlorides: The acid chloride (5 eq) is added in DCM, followed by pyridine (10 eq). Stirring is carried out at ambient temperature for 3 h and the resin is then washed. The following reactants are used: propanesulfonyl chloride and 2-thiophenesulfonyl chloride.

Isocyanates, isothiocyanate: the reactant (5 eq) is added in DCM, without base. Stirring is carried out at ambient temperature for 3 h and the resin is then washed. The following reactants are used: phenylethyl isocyanate and 4-acetylphenyl thioisocyanate.

Acids: the reactant (4 eq) is added in DMF, followed by HOBt (4 eq). Stirring is carried out at ambient temperature for 12 h and the resin is then washed. The following reactants are used: 2-thiopheneacetic acid and 2-pyridylacryloic acid.

Acid anhydrides: the reactant (2 eq) is added in DCM, followed by the DIEA (4 eq). Stirring is carried out at ambient temperature for 3 h and the resin is then washed. The following reactant is used: phenoxyacetic anhydride.

e) Cleavage

The kans are sorted in IRORI® cleavage blocks by means of the autosorter. The products are cleaved by adding 2 ml of 50/50 TFA/DCM solution. The cleavage solutions are filtered in pre-tared test pieces, and evaporated. Each product is redissolved in 1 ml of acetonitrile, from which a 50 µl aliquot is taken and transferred onto a 96-well plate for LC/MS analysis. The aliquot is diluted in 1 ml of $CH_3CN$/$H_2O$ solution and directly injected into LC/MS.

A combinatorial library of 810 (9×9×10) compounds that is useful for screening for these compounds as medicinal products is thus obtained.

Example 4

Synthesis of a Combinatorial Library (Rank 2; N=$R_3$ Double Bond). Combinatorial Library of Hydrazide-type Derivatives This synthesis is carried out in Irori® MiniKans. Each MiniKan contains 44 mg of resin, loaded at 1.12 mmol/g. 2 ml of solvent per MiniKan are envisioned during the reaction and the various washes. The latter are all carried out according to the following model:
twice with the reaction solvent
5 methanol/DCM cycles
once with ether.

The MiniKans are then dried under vacuum at 40° C. for 5 h.

a) First Randomization (Group $R_1$)

This is carried out in a variable manner according to the reactants used. Each reactor contains 21 MiniKans in 50 ml of the reaction solvent.

Isocyanates, isothiocyanate: the reactant (5 eq) is added in DCM. Stirring is carried out at ambient temperature for 2 h and the resin is then washed. The following reactants are used: ethyl isocyanate; 4-(trifluoromethyl)phenyl isocyanate; cyclopropyl isothiocyanate; phenyl isocyanate.

Carboxylic acids: the reactant (3 eq) and 993 mg of HOBt (6 eq, 135.13 g/mol) are added in DMF, followed by 1.15 ml of DIC (6 eq, 126.20 g/mol, 0.806). Stirring is carried out at ambient temperature overnight and the resin is then washed. The following reactants are used: 3-(1-cyanoethyl)benzoic acid; benzoic acid; 6-methylpicolinic acid; 3-(2-pyridyl) acrylic acid; pyrazinecarboxylic acid; benzofurazan-5-carboxylic acid; quinaldic acid; trans-2-hexenoic acid.

Acid anhydrides: the reactant (5 eq) is added in DCM, followed by 2.5 ml of DIEA (12 eq, 129.26 g/mol, 0.755). Stirring is carried out at ambient temperature for 4 h and the resin is then washed. The following reactants are used: valeric anhydride; isovaleric anhydride; 4-methoxybenzoic anhydride; methacrylic anhydride; 2-phenylbutyric anhydride; acetic anhydride.

Sulfonyl chlorides: the reactant (5 eq) is added in DCM, followed by 2.1 ml of DIEA (10 eq). Stirring is carried out at ambient temperature for 4 h and the resin is then washed. The following reactants are used: 2-naphthalenesulfonyl chloride; 2-mesitylenesulfonyl chloride; 2-thiophenesulfonyl chloride.

b) Formation of the Hydrazide

This is a common step. The 504 MiniKans are placed in 1.5 1 of hydrazine monohydrate (1/3)/DMF (2/3). Stirring is carried out at ambient temperature for 20 h and the resin is then washed with 2×DMF (1 1, then 2×MeOH (1 1), 3×DCM (1 1). The MiniKans are then dried.

c) Second Randomization (Group $R_3$)

Each reactor contains 24 MiniKans in 50 ml of THF/HC(OMe)$_3$ (1/1). Each aldehyde is added so as to obtain a concentration of 0.5 M. Heating is carried out at 60° C. for 18 h and the resin is then washed. The following reactants are used: 3-carboxybenzaldehyde; 3-methoxybenzaldehyde; 6-methoxy-2-naphthaldehyde; 4-nitrocinnamaldehyde; 4-cyanobenzaldehyde; 4-(methylmercapto)benzaldehyde; 4-(trifluoromethoxy)benzaldehyde; 3-pyridinecarboxaldehyde; 4-(1-pyrrolidino)benzaldehyde; 4-formyl-2-phenylimidazole; 1-methyl-2-imidazolecarboxaldehyde; 1-(phenylsulfonyl)-2-pyrrolecarboxaldehyde; 2-quinolinecarboxaldehyde; 4-(3-dimethylamino)propoxy)benzaldehyde; 2-butyl-4-formylimidazole; 6-fluoroveratraldehyde; 3-dimethylamino-2,2-dimethylpropionaldehyde; 2-furaldehyde; 3-pyrazolecarboxaldehyde; 2-(4-methoxyphenyl)benzofuran-7-carbaldehyde; 4-(5-formylfuran-2-yl)-benzenesulfonamide; 1-(4-chlorophenyl)pyrrole-2-carboxaldehyde; 2-[1-methyl-3-(trifluoromethyl)pyrazol-5-yl]thiophene-5-carboxaldehyde; 4-pyridine-4-carboxaldehyde.

d) Cleavage

The kans are sorted in IRORI® cleavage blocks by means of the autosorter. The products are cleaved by adding 2 ml of 50/50 TFA/DCM solution. The cleavage solutions are filtered in pre-tared test pieces, and evaporated. Each product is redissolved in 1 ml of acetonitrile, a 50 µl aliquot of which is taken and transferred onto a 96-well plate for LC/MS analysis. The aliquot is diluted in 1 ml of $CH_3CN$/$H_2O$ solution and directly injected into LC/MS.

A combinatorial library of 504 (21×24) compounds that is useful for screening for these compounds as medicinal products is thus obtained.

Pharmacological Study of the Compounds of the Invention

Study of the Inhibition of Cathepsin K

The test compounds (10 mM) are diluted to 1 mM in DMSO and distributed into Nunc polystyrene 96-well plates in a proportion of 2 μl per well. Column 12 of the plate is reserved for the controls and therefore receives 1 μl of DMSO (without product) per well. The plates are stored at −80° C. and thawed on the day of the experiment.

The compounds are diluted to 50 μM by adding 38 μl of reaction buffer: 100 mM sodium acetate, 5 mM EDTA, 1 mM DTT, pH 5.5. The addition and all the subsequent pipetting operations are carried out using a CybiWell 96-tip pipeter. After the solutions have been mixed, each product is transferred into 2 wells (duplicates) of a Greiner black 384-well plate, in a proportion of 10 μl per well. Two 96-well plates can therefore be tested in one 384-well plate.

A solution of substrate at 50 μM, Z-Val-arg-AMC (Calbiochem), is prepared in the reaction buffer. The substrate is then distributed into all the wells of the 384-well plate (20 μl per well).

A solution of cathepsin K at 12.5 ng/ml is prepared in the reaction buffer and distributed into all the wells of the 384-well plate (20 μl per well), except for the 16 wells serving as 100% inhibition controls (columns 23 and 24, rows I to P) which will receive 20 μl of buffer without enzyme. The 100% inhibition controls are performed in columns 23 and 24, rows A to H, which do not contain any compounds.

The plates are then incubated for 2H at ambient temperature, and then read on a Fluoroskan (Labsystems): excitation 390 nm; emission 460 nm.

The final concentrations of each of the reactants are: compounds 10 μM, substrate 20 μM, enzyme 5 ng/ml.

The % inhibition values for each of the compounds are calculated using the points at 0% and 100% inhibition of each plate as references. The compounds exhibiting a significant inhibition are then- retested over a concentration range of from 50 to 0.5 μM, in order to determine an $IC_{50}$.

The results show that the compounds according to the invention are active.

Example 6

Pharmaceutical Composition

Tablets corresponding to the following formula were prepared:

Compound according to the invention 500 mg Excipient for a tablet with a final weight of: 1 g (excipient in detail: lactose, talc, starch, magnesium stearate).

What is claimed is:

1. A compound of formula (I):

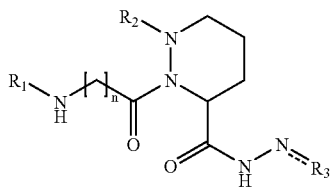

(I)

wherein
n is an integer from 0 to 6;
$R_1$ is selected from
C(O)—(CH$_2$)$_m$—R,
C(O)—NH—(CH$_2$)$_m$—R,
C(S)—NH—(CH$_2$)$_m$—R,
SO$_2$—(CH$_2$)$_m$—R,
  wherein m is an integer from 0 to 6, and when m is greater than 2 a double bond is optionally present;
R is selected from
  hydrogen when m is other than 0,
  hydroxyl,
  thiol,
  cyano,
  linear or branched alkoxy containing from 1 to 6 carbon atoms,
  aryloxy,
  aralkoxy,
  cycloalkyl having from 3 to 6 carbon atoms,
  a saturated or unsaturated monocyclic or bicyclic heterocyclic group,
    wherein the ring of the heterocyclic group is optionally substituted with one to three substituents independently selected from OH, SH, NH$_2$, NO$_2$, cyano, carboxyl, carbamoyl, halogen, trifluoromethyl, linear or branched alkyl containing from 1 to 6 carbon atoms, linear or branched alkoxy containing from 1 to 6 carbon atoms, acyl containing from 2 to 6 carbon atoms, aryl, aralkyl, or a saturated or unsaturated monocyclic or bicyclic heterocycle,
    wherein said alkyl, aryl, aralkyl or heterocycle is each optionally substituted with one to three substituents independently selected from OH, SH, NH$_2$, NO$_2$, cyano, carboxyl, carbamoyl, halogen, or trifluoromethyl;
  aryl containing from 6 to 10 carbon atoms or aralkyl containing from 7 to 11 carbon atoms,
    wherein the ring of said aryl or aralkyl is each optionally substituted with one to three substituents independently selected from OH, SH, NH$_2$, NO$_2$, cyano, carboxyl, carbamoyl, halogen, trifluoromethyl, linear or branched alkyl containing from 1 to 6 carbon atoms, linear or branched alkoxy containing from 1 to 6 carbon atoms, acyl containing from 2 to 6 carbon atoms or a saturated or unsaturated monocyclic or bicyclic heterocycle,
    wherein said alkyl or heterocycle is each optionally substituted with one to three substituents independently selected from OH, SH, NH$_2$, NO$_2$, cyano, carboxyl, carbamoyl, halogen or trifluoromethyl; or
  NR$_4$R$_5$ wherein R$_4$ is hydrogen or a linear or branched alkyl group having from 1 to 6 carbon atoms, and R$_5$ is hydrogen, a linear or branched alkyl radical having from 1 to 6 carbon atoms, or an aryl group;
R$_2$ is hydrogen or is as defined for R$_1$, wherein R$_2$ and R$_1$ are identical or different;
N=R$_3$ is NH—R$_3$ or N=R$_3$,
  when N=R$_3$ is NH—R$_3$, R$_3$ is as defined for R$_1$
    wherein R$_3$ and R$_1$ are identical or different, and
  when N=R$_3$ is N=R$_3$, R$_3$ is as defined for R
    wherein R$_3$ and R are identical or different; or
an enantiomer, a racemate, a diastereoisomer, or a mixture in any combination thereof, or a pharmaceutically acceptable salt thereof.

2. The compound according to claim 1 wherein n is 2.

3. The compound according to claim 1 wherein R$_2$ is hydrogen.

4. The compound according to claim 3 wherein n is 2.

5. The compound according to claim 1 wherein N=R$_3$ is NH—R$_3$.

6. The compound according to claim 5 wherein n is 2.

7. The compound according to claim 6 wherein $R_2$ is hydrogen.

8. The compound according to claim 1 wherein N=$R_3$ is N=$R_3$.

9. The compound according to claim 8 wherein n is 2.

10. The compound according to claim 9 wherein $R_2$ is hydrogen.

11. The compound according to claim 1 having the stereochemistry

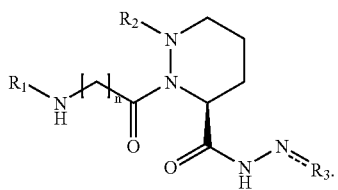

12. A pharmaceutical composition comprising a pharmaceutically acceptable carrier and a compound of formula I according to claim 1, or a stereoisomer, an enantiomer, a racemate, a diastereoisomer, or a mixture in any combination thereof, or a pharmaceutically acceptable salt thereof.

13. A process for preparing a compound of formula I according to claim 1 comprising the steps of:

(i) coupling a compound of formula (II)

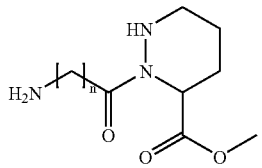

wherein n is as defined in claim 1 and an immobilized support to form an immobilized compound of formula (III)

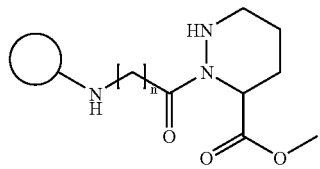

wherein a circle denotes the support;

(ii) reacting the compound of formula (III) with a compound of formula $R_1'$ to form a compound of formula (IV)

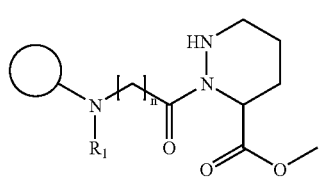

wherein the compound $R_1'$ is a precursor of $R_1$, and $R_1$ and n is each as defined in claim 1;

(iii) optionally reacting the compound of formula (IV) with a compound of formula $R_2'$ to form a compound of formula (V)

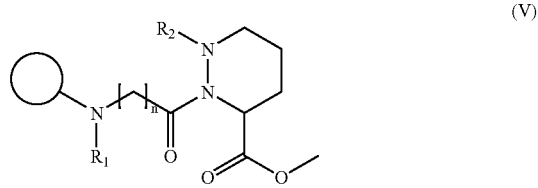

wherein the compound $R_2'$ is a precursor of $R_2$, and $R_2$ and n is each as defined in claim 1;

(iv) reacting the compound of formula (IV) or formula (V) with hydrazine to form a compound of formula (VI)

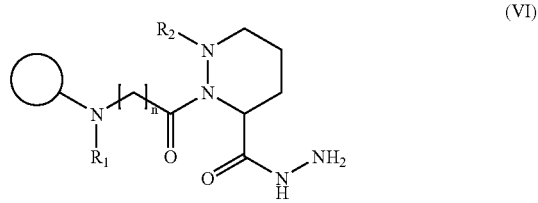

wherein $R_1$, $R_2$ and n is each as defined in claim 1;

(v) reacting the compound of formula (VI) with a compound of formula $R_3'$ to form a compound of formula (VII)

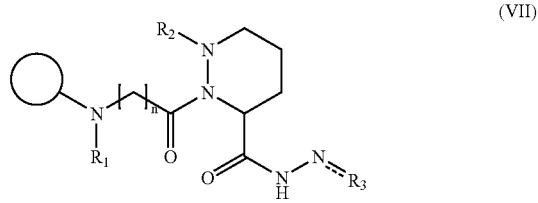

wherein the compound $R_3'$ is a precursor of $R_3$, and $R_3$ and n is each as defined in claim 1;

(vi) cleaving the compound of formula (VII) from the support to provide a compound of formula (I)

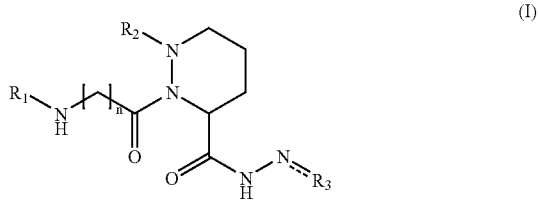

wherein $R_1$, $R_2$, $R_3$ and n is each as defined in claim 1.

14. The process according to claim 13 wherein the compound $R_1'$ and $R_2'$ is each independently selected from the group consisting of an isocyanate, an isothiocyanate, a carboxylic acid, an acid anhydride, a sulfonyl chloride, a carbamoyl chloride, an acid chloride and a chloroformate.

15. The process according to claim 13 wherein compound $R_3'$ is selected from the group consisting of an isocyanate, an isothiocyanate, a carboxylic acid, an acid anhydride, a sulfonyl chloride, a carbamoyl chloride, an acid chloride and a chloroformate when $N=R_3$ is $NH-R_3$.

16. The process according to claim 13 wherein compound $R_3'$ is an aldehyde when $N=R_3$ is $N=R_3$.

17. The process according to claim 13 comprising simultaneously or sequentially performing the steps of said process on a plurality of reactants.

18. The process according to claim 17 wherein compound $R_2'$ is an acid chloride.

19. The process according to claim 18 wherein compound $R_1'$ is selected from the group consisting of an isocyanate, an isothiocyanate, a carboxylic acid, an acid anhydride and a sulfonyl chloride.

20. The process according to claim 19 wherein compound $R_3'$ is selected from the group consisting of an isocyanate, an isothiocyanate, a carboxylic acid, an acid anhydride, a sulfonyl chloride and an acid chloride.

21. The process according to claim 17 wherein $R_2$ is hydrogen.

22. The process according to claim 21 wherein compound $R_1'$ is selected from the group consisting of an isocyanate, an isothiocyanate, a carboxylic acid, an acid anhydride and a sulfonyl chloride.

23. The process according to claim 22 wherein compound $R_3'$ is an aldehyde.

* * * * *